United States Patent [19]
McKellar et al.

[11] Patent Number: 5,744,494
[45] Date of Patent: Apr. 28, 1998

[54] SYNERGISTIC COMPOSITIONS CONTAINING BENZIMIDAZOLE ANTHELMINTICS AND METHYLENEDIOXYPHENYL COMPOUNDS

[75] Inventors: Quintin Archibald McKellar, Lochwinnoch; Hafid Abdelaali Benchaoui, Glasgow, both of United Kingdom

[73] Assignee: British Technology Group Limited, London, England

[21] Appl. No.: 495,486

[22] PCT Filed: Feb. 2, 1994

[86] PCT No.: PCT/GB94/00193

§ 371 Date: Jul. 25, 1995

§ 102(e) Date: Jul. 25, 1995

[87] PCT Pub. No.: WO94/17798

PCT Pub. Date: Aug. 18, 1994

[30] Foreign Application Priority Data

Feb. 3, 1993 [GB] United Kingdom ............... 9302107

[51] Int. Cl.$^6$ .................... A61K 31/415; A61K 31/36
[52] U.S. Cl. ................ 514/388; 514/387; 514/464
[58] Field of Search .................. 514/388, 464, 514/387

[56] References Cited

U.S. PATENT DOCUMENTS 5,135,953  8/1992  Potter et al. ................... 514/594

FOREIGN PATENT DOCUMENTS 0 512 379 A1  11/1992  European Pat. Off..
2 250 022  5/1992  United Kingdom.

OTHER PUBLICATIONS

Y. Tada et al. "Acute renal toxicity of the thiabendazole..." Food Chem. Toxic., vol. 30, No. 12, 1992, pp. 1021–1030.

T. Mizutani et al. "Nephrotoxicity of thiabendazole in mice..." Food Chem. Toxic., vol. 28 No. 3, 1990, pp. 169–177.

Isshiki K. et al. "Effects of post-harvest fungicides..." J. Food Hyg. Soc. Jpn., vol. 24 No. 3, 1983, pp. 268–274.

*Primary Examiner*—Marianne M. Cintins
*Assistant Examiner*—M. Moezie
*Attorney, Agent, or Firm*—Nixon & Vanderhye

[57] ABSTRACT

The anthelmintic efficacy in animals and humans of a benzimidazole such as fenbendazole, albendazole, oxfendazole or trichlabendazole is potentiated by use with piperonyl butoxide or other methylenedioxyphenyl synergist.

14 Claims, 2 Drawing Sheets

SYNERGISTIC COMPOSITIONS CONTAINING BENZIMIDAZOLE ANTHELMINTICS AND METHYLENEDIOXYPHENYL COMPOUNDS

This application is a 3.71 of PCT/GB94/00193 filed Feb. 2, 1994.

The present invention relates to pharmaceutical compositions comprising benzimidazole anthelmintic agents, particularly though not exclusively for veterinary use, and potentiation thereof by means of piperonyl butoxide or other methylenedioxyphenyl insecticide synergist.

BACKGROUND OF THE INVENTION

Benzimidazoles are a well known class of anthelmintic agents which are widely used for the control of endoparasites, particularly nematodes, in domestic and agricultural animals. Albendazole is indicated for use in humans. Whilst these agents have been used successfully, a number of these anthelmintic benzimidazoles are degraded by oxidative mechanisms in vivo, which accelerates their excretion and this may limit their efficacy and may mean that periodic administrations are necessary.

Furthermore, certain parasites may be resistant to particular benzimidazoles.

Piperonyl butoxide is a well known insecticide synergist (see Merck Index 7446). This and other methylenedioxyphenyl insecticide synergists have been widely used in conjunction with pyrethroid insecticides.

It has been reported (Food Chem. Toxicol. (1992 December); 30(12), 1021–30) that the acute toxic effects of the benzimidazole thiabendazole on the kidneys of mice are enhanced by pretreatment with inhibitors of the microsomal monooxygenase system viz 2-diethylaminoethyl-2,2-diphenylvalerate hydrochloride and piperonyl butoxide. The reference is limited to a consideration of toxicity and does not disclose any effects regarding the anthelmintic efficacy of the treatments.

DESCRIPTION OF THE INVENTION

Generally speaking, the present invention relates to the discovery that the anthelmintic effects of benzimidazoles may be enhanced by co-administration with a methylenedioxyphenyl insecticide synergist such as piperonyl butoxide.

Thus, the present invention particularly provides a pharmaceutical composition which comprises an anthelmintically effective amount of a benzimidazole or pro-drug thereof together with a methylenedioxyphenyl synergist.

The benzimidazole is particularly one subject to oxidative degradation in vivo. Where the benzimidazole contains a thio group, oxidation in vivo generally proceeds via the sulphoxide metabolite (which may also have anthelmintic activity) to the inactive sulphone.

Another oxidative mechanism involves hydroxylation for example at the 5-position on the benzimidazole ring.

The invention also relates to the use of a methylenedioxyphenyl synergist to potentiate such benzimidazole or pro-drug thereof.

Furthermore, the invention includes methods of treating animals and humans for the treatment of endoparasitic infections by the administration of the benzimidazole or pro-drug thereof together with a methylenedioxyphenyl synergist.

The methylenedioxyphenyl synergist is an inhibitor of the hepatic cytochrome P450 system. Many such insecticide synergists (which have no anthelmintic or pesticidal activity themselves) are known as synergists of the pyrethroid group of insecticides and these are generally encompassed by the present invention. Specific synergists include piperonyl butoxide, piperonyl cyclonene, carboxyethyl piperonyl cyclonene, sesamine, n-propyl isome, and sulfoxide (chemical name 1,2-(methylenedioxy)-4-[2-(octyl sulfinyl) propyl]benzene).

The pharmaceutical composition may include a pharmaceutically acceptable inert carrier or diluent appropriate to the method of administration. Thus, the composition may be administered orally or parenterally (including subcutaneous, intramuscular and intravenous injection). For oral administration, the pharmaceutical compositions may be presented as a drench, such as a solution or suspension in water. The drench may include as appropriate suspending agents, preserving agents, thickening agents or emulsifying agents according to well known formulation techniques. Oral administration may also be by way of incorporation of the composition into foodstuff or as a feedblock. The composition may also be formulated as pellets or granules. Particularly for human administration, the composition may be formulated as a solid unit dose form (e.g. a tablet, capsule or cachet) or as a liquid unit dose form (e.g. as a liquid-containing capsule).

The composition may be administered to a ruminant animal as an intraruminal bolus, which is retained in the rumen of the ruminant animal and delivers the composition over a prolonged period of time. Suitable intraruminal boluses are well known in the art.

For parenteral administration, the composition may be presented as a sterile solution or suspension and may contain preservatives and other materials for rendering the composition isotonic with the blood of the intended recipient. Such compositions may conveniently be presented in unit-dose or multi-dose sealed containers.

The composition may also be formulated for topical administration (for example, as a paste, viscous liquid, or gel) or as a so-called pour-on formulation, wherein the active agents pass through the skin.

The composition may also be formulated for rectal, nasal or vaginal administration.

The benzimidazole may be administered together with the methylenedioxyphenyl synergist in a single composition, or the benzimidazole and methylenedioxyphenyl synergist may be administered separately at close time intervals such that the two agents become mixed in the body of the recipient.

Alternatively, the composition may be administered in other ways conventional for anthelmintic administration.

The benzimidazole will generally be administered in non-toxic conventional dosage amounts, though these may be reduced in accordance with the potentiation caused by the methylenedioxyphenyl synergist. Typically, the benzimidazole is administered in a dosage of 1 to 50 mg/kg based on the body weight. Again, the amount of methylenedioxyphenyl synergist present will depend on its own potency and on the nature of the benzimidazole but is usually in the range 0.01–0.5 g/kg body weight. Usually, the ratio of methylenedioxyphenyl synergist to benzimidazole is in the region 10–500 to one, particularly 30–120 to one on a weight to weight basis.

Benzimidazoles may be sub-divided into various groups, such as those including a thio group, those including a sulphoxide group, those including an ether group, and those which are carbamic acid methyl esters. Benzimidazoles including a thiazolyl group (such as thiabendazole and cambendazole) are less preferred.

The benzimidazole is generally one which is subject to oxidative degradation in vivo and it is believed that the piperonyl butoxide or other methylenedioxyphenyl synergist acts to mitigate this oxidative degradation, thereby enhancing blood plasma levels of the benzimidazole and possibly prolonging its residence time. Particularly preferred benzimidazoles and prodrugs thereof include netobimin, febantel, albendazole, albendazole sulphoxide, fenbendazole, oxfendazole, triclabendazole, triclabendazole sulphoxide, thiabendazole, cambendazole, oxibendazole and luxabendazole.

The composition is particularly though not exclusively for veterinary use and typical animals include domestic and agricultural animals, particularly ruminants, and especially pigs, goats, horses, cattle, sheep, dogs, cats, and poultry.

The composition is also suitable for human use, particularly against resistant endoparasites. An especially useful composition for gastrointestinal infestations comprises albendazole or albendazole sulfoxide, together with piperonyl butoxide.

The composition is effective against helminth endoparasites, particularly gastrointestinal nematodes, cestodes and trematodes. Specific examples include hookworms, ascariasis, enterobiasis, strongyloidiasis, and trichuriasis.

The term pro-drug as used herein is a well known term of art which means an agent which is not in itself necessarily active, but which becomes converted in vivo to an anthelmintically active metabolite. Netobimin and febantel are pro-drugs which are converted into benzimidazoles in vivo.

BRIEF DESCRIPTION OF THE DRAWINGS

The invention will now be described with reference to the accompanying drawings, in which.

Embodiments of the present invention will now be described by way of example only.

EXAMPLES

Example 1 (fenbendazole)

In order to minimise interindividual variations our experimental protocol was designed as a crossover (each animal was used as its own control). A five week wash-out period was allowed between crossovers. Six goats were used in this experiment.

First period: Fenbendazole (Panacur 2.5%) was administered orally at a dose rate of 7.5 mg/kg. Blood samples were taken prior to drug administration and 0.25, 0.5, 1, 2, 4, 8, 12, 24, 32, 48, 72 and 96 hours thereafter.

Second period: One hour before administration of fenbendazole (7.5 mg/kg) the animals received a dose of piperonyl butoxide (0.5 g/kg) given intramuscularly. Blood samples were taken as in the first period.

Plasma samples were analysed for fenbendazole by High Performance Liquid Chromatography.

As can be seen from Table 1 the use of piperonyl butoxide in combination with fenbendazole resulted in a significant increase of the area under the plasma concentration-time curve (AUC) and also in a significantly prolonged residence time for fenbendazole.

Figure 1:
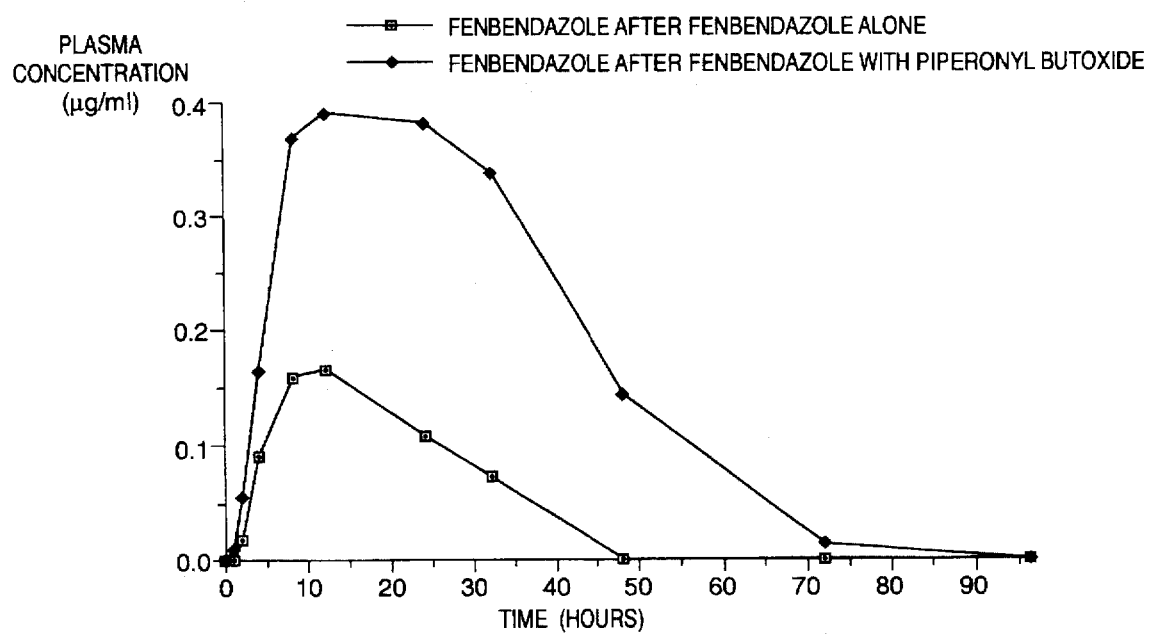
FIG. 1 shows plasma concentrations of fenbendazole following administration of fenbendazole alone (squares) or together with piperonyl butoxide (diamonds)

FIG. 1 shows plasma concentrations of fenbendazole following administration of fenbendazole alone (squares) or together with piperonyl butoxide (diamonds).

Figure 2:
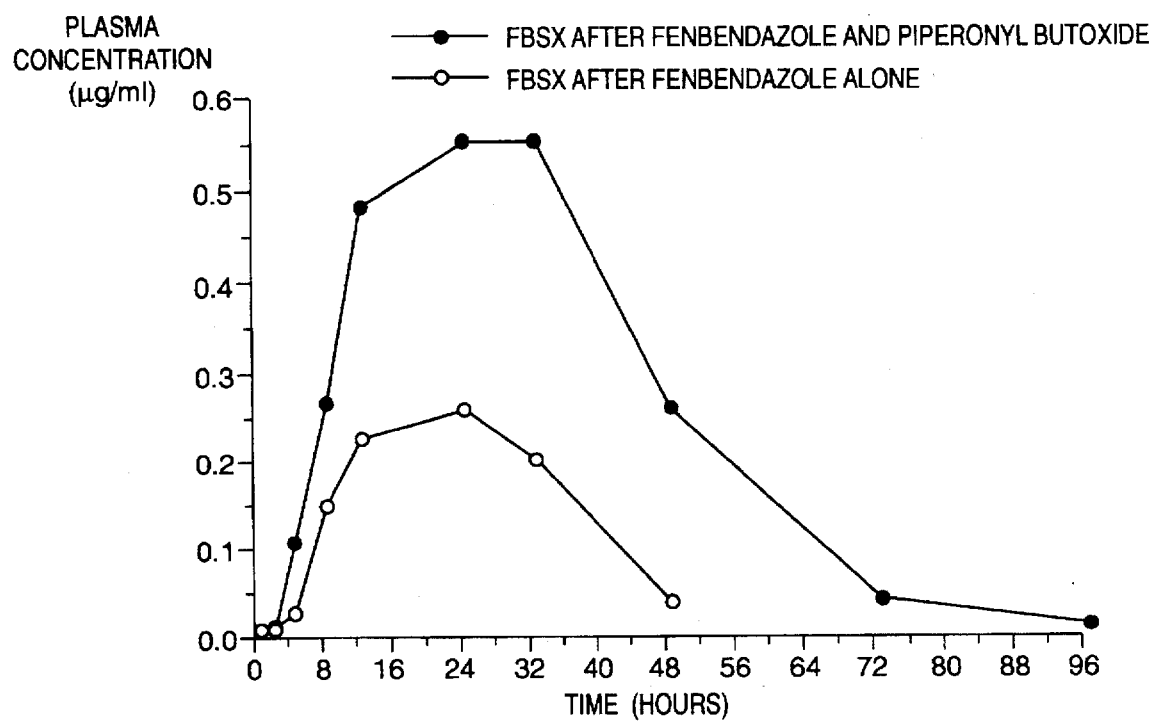
FIG. 2 shows corresponding levels of the active metabolite fenbendazole sulphoxide after administration of fenbendazole alone (open circles) and together with piperonyl butoxide (closed circles)

FIG. 2 shows the corresponding levels of the active metabolite fenbendazole sulfoxide after administration of fenbendazole alone (open circles) and together with piperonyl butoxide (closed circles).

Example 2 (albendazole)

Five sheep were used in this experiment.

The same protocol as described above except that the anthelmintic used was albendazole (Valbazen 2.5%) given at a dose rate of 7.5 mg/kg. Plasma samples were analysed for the metabolite albendazole sulfoxide by High Performance Liquid Chromatography.

Figure 3:
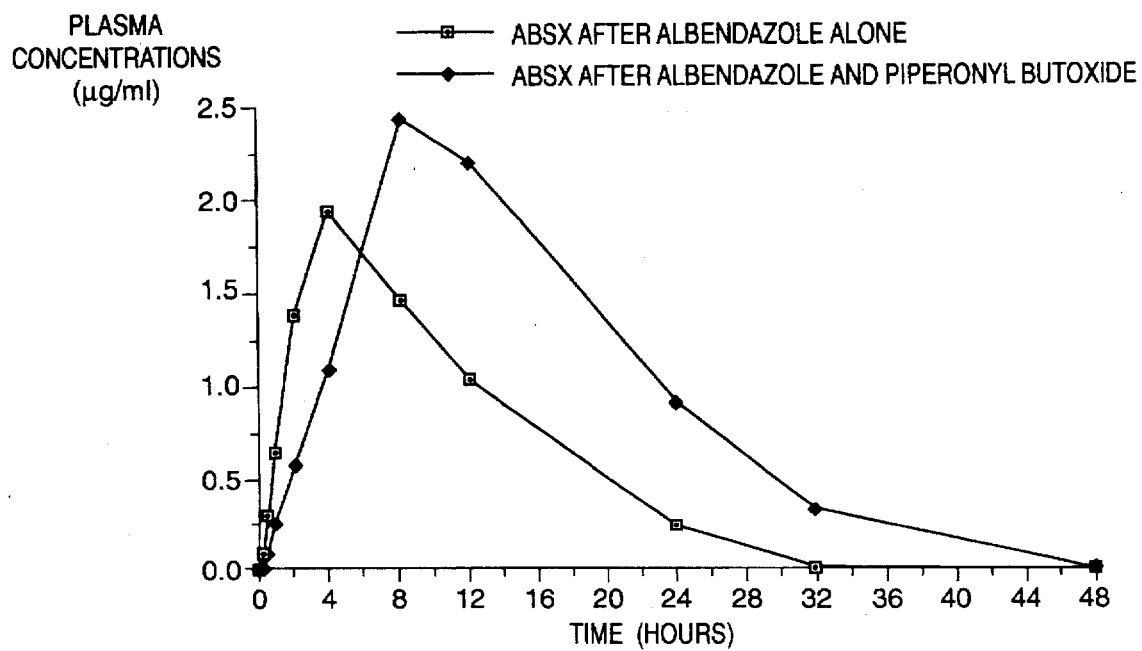
FIG. 3 shows plasma concentrations of albendazole sulphoxide (active metabolite) following administration of albendazole alone (squares) or together with piperonyl butoxide (diamonds).

The results are shown in Table 1 and in FIG. 3.

FIG. 3 shows plasma concentrations of albendazole sulfoxide (active metabolite) following administration of albendazole alone (squares) or together with piperonyl butoxide (diamonds).

TABLE 1

| | Area under plasma-concentration-time curve (ug · h/ml) | |
|---|---|---|
| Active Agent | Active alone | Active plus piperonyl butoxide |
| Fenbendazole | 4.17 | 16.57 |
| Fenbendazole sulfoxide | 7.72 | 22.90 |
| Albendazole sulfoxide | 25.61 | 45.41 |

Example 3 (dose optimisation)

A six-phase experiment was carried out to determine the optimal concentration ratio of piperonyl butoxide: fenbendazole.

Six one year old blackface sheep were administered fenbendazole (Panacur 2.5%) orally at a fixed dose of 5 mg/kg on six occasions. Piperonyl butoxide was administered concurrently by stomach tube according to the protocol outlined in Table 2. This meant that each sheep had received 0, 15, 31, 63, 125 and 250 mg/kg piperonyl butoxide in combination with the benzimidazole.

A similar sampling protocol to that used in Example 1 was used and a 4 week wash out was allowed between each phase of the study.

Analysis of all combination ratios in a single animal were carried out, and a target dosage ratio of 63 mg/kg piperonyl butoxide: 5 mg/kg fenbendazole (ratio 12.6 to 1) thereby obtained.

At the end of this study all animals were killed and a thorough gross and histopathological examination carried out. There were no abnormal gross lesions. The results of the histopathological study showed no significant overdose of toxicity.

Example 4 (efficacy)

A study was carried out to determine the efficacy of the piperonyl butoxide: fenbendazole combination and to compare it with piperonyl-butoxide and fenbendazole alone against benzimidazole resistant abomasal parasites.

Twenty-four parasite naive Suffolk cross lambs were allocated into four groups of six. Each lamb received an oral dose of 6,000 benzimidazole resistant *Ostertagia circumcincta* and 2,400 benzimidazole resistant *Haemonchus contortus*.

Twenty-eight days after infection animals were treated as follows:

| Group 1 | No treatment |
|---|---|
| Group 2 | Piperonyl butoxide (63 mg/kg) by stomach tube. |
| Group 3 | Fenbendazole (5 mg/kg) by stomach tube. |
| Group 4 | Piperonyl butoxide (63 mg/kg) and fenbendazole (5 mg/kg) by stomach tube. |

Blood samples were collected from all animals according to the protocol used in Example 1.

All lambs were faecal sampled and killed seven days after treatment (day 35). Nematode egg numbers were determined in faeces by the McMaster egg counting technique (Gordon and Whitlock (1939) J. Council for Scientific and Industrial Res., 12,50) and numbers of *O. circumcincta* were determined by the dilution method of Ritchie et al. (1966), Amer J. Vet. Res., 27, 659–667. Total abomasal counts of *H. contortus* were determined.

The results demonstrated a 79.7% and 98.4% reduction in faecal egg counts in the fenbendazole alone and piperonyl butoxide plus fenbendazole treated groups respectively (Table 3). The combination was significantly (P<0.05) more effective at reducing faecal egg count than fenbendazole alone.

Neither piperonyl butoxide nor fenbendazole alone significantly reduced the number of *O.circumcincta* present in the abomasa of sheep at necropsy. The combination product, however, reduced the burden of *O.circumcincta* by 84.9% (Table 4).

Both fenbendazole alone and the combination product significantly reduced the numbers of *H.contortus* at necropsy. However, the combination was significantly (P<0.005) more effective than fenbendazole alone. Piperonyl butoxide alone had no effect (Table 5).

Example 5 (hepatocyte studies)

An experiment using hepatocytes cultured from rats has been initiated to determine the metabolic interactions of piperonyl butoxide and fenbendazole (50 micromoles). The concentration of fenbendazole in cell culture medium was about 2 micrograms/ml when fenbendazole was administered alone. Much higher concentrations of fenbendazole (about 3.7 micrograms/ml) were maintained when co-administered with piperonyl butoxide. Concentrations of the sulfoxide and sulfone metabolites were much reduced in the presence of piperonyl butoxide. It was concluded from this that piperonyl butoxide was inhibiting the oxidative metabolism of fenbendazole by rat liver cells.

Example 6

The procedure of Example 5 was repeated using oxfendazole, and similar results were obtained.

Example 7

The procedure of Example 5 was repeated using albendazole, and similar results were obtained.

Example 8

The procedure of Example 5 was repeated using triclabendazole, and similar results were obtained.

TABLE 2

Dosing Protocol for titration experiment (Experiment 3) to determine the optimum ratio of piperonyl butoxide:fenbendazole.

| Crossover | Sheep 1 | Sheep 2 | Sheep 3 | Sheep 4 | Sheep 5 | Sheep 6 |
|---|---|---|---|---|---|---|
| 1 | 0 | 250 | 125 | 63 | 125 | 250 |
| 2 | 15 | 0 | 250 | 31 | 63 | 125 |
| 3 | 31 | 15 | 0 | 15 | 31 | 63 |
| 4 | 63 | 31 | 15 | 0 | 1 | 31 |
| 5 | 125 | 63 | 31 | 250 | 0 | 1 |
| 6 | 250 | 125 | 63 | 125 | 250 | 0 |

TABLE 3

Mean ±SD faecal egg counts in sheep seven days after treatment.

| | | Eggs per gram of faeces |
|---|---|---|
| Group 1 | No treatment | 491 ± 267 |
| Group 2 | Piperonyl butoxide | 483 ± 342 |
| Group 3 | Fenbendazole | 100 ± 84* |
| Group 4 | Piperonyl butoxide plus Fenbendazole | 8 ± 20** |

Significantly (P < 0.005** p < 0.05*) different from group 1 controls by analysis of variance.

TABLE 4

Mean ±SD numbers of *O. circumcincta* in sheep killed 7 days after treatment.

| | | Number of *O. circumcincta* |
|---|---|---|
| Group 1 | No treatment | 2985 ± 654 |
| Group 2 | Piperonyl butoxide | 3783 ± 441 |
| Group 3 | Fenbendazole | 2875 ± 1308 |
| Group 4 | Piperonyl butoxide plus Fenbendazole | 450 ± 565 |

Significantly, (P<0.001) different from group 1 controls by analysis of variance.

TABLE 5

Mean ±SD numbers of *H. contortus* in sheep killed 7 days after treatment.

| | | Number of *H. contortus* |
|---|---|---|
| Group 1 | No treatment | 345 ± 69 |
| Group 2 | Piperonyl butoxide | 320 ± 133* |
| Group 3 | Fenbendazole | 58 ± 29 |
| Group 4 | Piperonyl butoxide plus fenbendazole. | 7 ± 8* |

Significantly, (P<0.001) different from group 1 controls by analysis of variance.

We claim:

1. A pharmaceutical composition which comprises an anthelmintically effective amount of a benzimidazole or pro-drug thereof together with
   a methylenedioxyphenyl synergist;
   provided that the benzimidazole anthelmintic is not thiabendazole.

2. A composition according to claim 1 wherein the benzimidazole contains a thio group.

3. A composition according to claim 2 wherein the benzimidazole is selected from the group consisting of albendazole, fenbendazole, and triclabendazole.

4. A composition according to claim 1 wherein the benzimidazole contains a sulphoxide group.

5. A composition according to claim 4 wherein the benzimidazole is selected from the group consisting of albendazole sulphoxide, oxfendazole, and triclabendazole sulphoxide.

6. A composition according to claim 1 wherein the benzimidazole is a carbamic acid methyl ester.

7. A composition according to claim 6 wherein the benzimidazole is selected from the group consisting of albendazole, albendazole sulphoxide, fenbendazole, oxfendazole, oxibendazole, and luxabendazole.

8. A composition according to claim 1 wherein the benzimidazole pro-drug is selected from the group consisting of netobimin and febantel.

9. A composition according to claim 1 wherein the methylenedioxyphenyl synergist is selected from the group consisting of piperonyl butoxide, piperonyl cyclonene, carboxyethyl piperonyl cyclonene, sesamine, n-propyl isome, and sulfoxide.

10. A composition according to claim 1 wherein the ratio of benzimidazole or pro-drug thereof to methylenedioxyphenyl synergist is about 1:10–500 on a weight basis.

11. A composition according to claim 1 which further comprises a pharmaceutically acceptable carrier.

12. A method of anthelmintic treatment of a human or animal, which comprises administering thereto an anthelmintically effective amount of a benzimidazole or pro-drug thereof together with a methylenedioxyphenyl synergist.

13. A method according to claim 12 wherein the benzimidazole is administered in a dosage of 1 to 50 mg/kg based on the human or animal bodyweight.

14. A method according to claim 12 wherein the methylenedioxyphenyl synergist is administered in a dosage of 0.01 to 0.5 g/kg based on the human or animal bodyweight.

* * * * *